United States Patent [19]

Hunt et al.

[11] Patent Number: 4,882,165
[45] Date of Patent: Nov. 21, 1989

[54] LIGHT SENSITIVE LIPOSOMES

[75] Inventors: C. Anthony Hunt; Charles Pidgeon, both of San Francisco, Calif.

[73] Assignee: The Regents of the University of California, Oakland, Calif.

[21] Appl. No.: 926,877

[22] Filed: Nov. 5, 1986

Related U.S. Application Data

[63] Continuation of Ser. No. 319,294, Nov. 9, 1981, abandoned.

[51] Int. Cl.$^4$ .......................... A61K 37/22; A61J 5/00; B01J 13/02; B32B 5/16
[52] U.S. Cl. ..................................... 424/450; 264/4.1; 264/4.3; 264/4.6; 428/402.2
[58] Field of Search .................... 252/316, 30; 424/38; 428/402.2; 264/4.1, 4.3, 4.6

[56] References Cited

U.S. PATENT DOCUMENTS

| | | | |
|---|---|---|---|
| 3,993,754 | 11/1976 | Rahmam et al. | 424/177 |
| 4,016,290 | 4/1977 | Rahman | 424/319 |
| 4,199,565 | 4/1980 | Fullerton | 424/89 |
| 4,235,871 | 11/1980 | Papahadjopoulos | 424/19 |
| 4,241,046 | 12/1980 | Papahadjopoulos | 424/19 |
| 4,331,654 | 5/1982 | Morris | 424/38 |
| 4,356,167 | 10/1982 | Kelly | 424/38 |

FOREIGN PATENT DOCUMENTS 2103485 2/1983 United Kingdom.

OTHER PUBLICATIONS

Pidgeon, C. and Hunt, C. A., "Photosomes: Light Sensitive Liposomes", p. 88 of Abstracts published by the American Pharmaceutical Assoc. on Sep.–Oct., 1980.
Delmelle, M., *Photochem. Photobiol.*, 28:357–360 (1978).
Warner et al., *J. Lipid Research*, 18, pp. 548–551 (1977).
Patel et al., *J. Lipid Research*, 20, pp. 674–677 (1979).
Kremer et al., *Biochem.*, 16, No. 17, pp. 3932–3935 (1977).
Hellingwerf et al., *Biochimica Biophysica Acta*, 547, pp. 544–582 (1979).
Delwelle, Protochem Photobiol, 28:357–360 (1978).
CA 95:49342p αTocopherol Retards Auto Oxidation and Prolongs Shelf Life of Liposomes.

*Primary Examiner*—Douglas W. Robinson
*Attorney, Agent, or Firm*—Majestic, Parsons, Siebert & Hsue

[57] ABSTRACT

Light sensitive liposomes are provided which release their contents on demand in response to irradiation with an appropriate wavelength of light. Substantially all the liposome contents can be released within about 60 seconds.

Preferred embodiments of the light sensitive liposomes include lipids having at least one retinoyl group and being a structural component of the lipid membrane.

15 Claims, No Drawings

LIGHT SENSITIVE LIPOSOMES

This is a continuation of application Ser. No. 319,294, filed Nov. 9, 1981, now abandoned.

BACKGROUND OF THE INVENTION

1. Field of the Invention

The present invention relates generally to liposomes, and more particularly to liposomes which encapsulate fluid materials, such as drugs, nucleic acids, proteins and the like, and which selectively release the fluid contents thereof in response to irradiation with light.

2. Prior Art

Liposomes are unilamellar or multilamellar lipid vesicles which enclose a 3-dimensional space. They are well recognized as useful for encapsulating therapeutic agents, such as cytotoxic drugs or other macromolecules capable of modifying cell behaviour, and carrying these agents to in vivo sites. For example, U.S. Pat. No. 3,993,754, inventors Rahman et al, issued Nov. 23, 1976, discloses an improved method for chemotherapy of malignant tumors in which an antitumor drug is encapsulated within liposomes and the liposomes are injected into an animal or man. Drug administration via liposomes can have reduced toxicity, altered tissue distribution, increased drug effectiveness, and an improved therapeutic index.

Liposomes have also been used in vitro as valuable tools to introduce various chemicals, biochemicals, genetic material and the like into viable cells. However, a serious deficiency of liposomal drug delivery has been the inability to quantitatively or selectively direct the liposomes' contents to specific sites of action over a therapeutically meaningful time frame. Use of temperature sensitive liposomes has been proposed as a possible solution to the problem. For example, temperature sensitive liposomes have been suggested for in vivo use to release methotrexate to particular sites in mice by heating the area where drug delivery was desired.

The present invention is directed to overcoming one or more of these problems.

SUMMARY OF THE INVENTION

Accordingly, it is an object of the present invention to provide liposomes which encapsulate fluids and which selectively release the fluids when irradiated with light.

It is another object of the present invention that such selective release of the liposomes' contents be finely tuned to an intensity and predetermined wavelength of light.

It is yet a further object of the present invention that liposomes be capable of releasing substantially their entire contents within about one minute of sufficient irradiation with light of a predetermined wavelength.

In one aspect of the present invention, a light sensitive liposome comprises a liquid membrane surrounding a fluid to define an encapsulating position of the lipid membrane for the fluid. The lipid membrane includes a light sensitive lipid which absorbs light at a predetermined wavelength so as to form a modified light sensitive lipid in response to sufficient light at the predetermined wavelength. The modified light sensitive lipid adjusts the lipid membrane from the encapsulating position to a releasing position. In the releasing position the fluid communicates with the medium, or environment, outside the lipid membrane.

The inventive light sensitive liposomes may be used, for example, to selectively deliver a fluid to cell cultures. Thus, the inventive light sensitive liposomes may be introduced into one or more cell cultures, and irradiated when desired with sufficient light to release the fluid on demand. The fluid released may include various chemicals, biochemicals, genetic material or the like.

DETAILED DESCRIPTION OF THE PREFERRED EMBODIMENTS

Generally, and as well known, the lipid membranes of liposomes are formed by a bimolecular layer of one or more lipid compounds having polar heads and nonpolar tails. In an aqueous solution, the polar heads of one layer orient outwardly to extend into the aqueous solution and to form a continuous, outer surface. The polar heads of the other layer orient to extend into an aqueous, or polar liquid, phase of the fluid surrounded, or encapsulated, by the bimolecular layer. The nonpolar tails of each layer form a continuous, hydrocarbon phase therebetween.

Both naturally occurring and synthetic lipids are known as useful in forming liposomes. For example, naturally occurring lipids such as phosphoglycerides, sphingolipids, and glycolipids are all characterized by having polar head regions and nonpolar tail regions which form bimolecular layers readily in aqueous systems. A variety of synthetic lipids (often differing from the naturally occurring lipids simply by having different hydrocarbon chain lengths in the nonpolar tail regions) are also known and have been used to form liposomes. In addition, components such as Vitamin E (normally considered to be lipid since it is insoluble in water but extractable with organic solvents) and the like may be included in liposome membranes.

The inventive light sensitive liposomes may be formed from one or more starting lipids by any of the various conventional techniques. These various conventional techniques may be generally characterized as yielding unilamellar vesicles or multilamellar vesicles. Either liposomal structure is suitable for the present invention; however, the unilamellar structure is normally preferred due to the generally larger internal space available for the encapsulated fluid.

The fluid encapsulated by the light sensitive liposomes includes a polar liquid, or aqueous, phase into which the polar heads of the membrane's inner layer extend. The fluid may carry, either dissolved or undissolved, a wide variety of other components. For example, the fluid may include biologically active molecules, pharmaceuticals, nutrients, radioactive ions, chemiluminescers and fluorescers.

Light sensitive liposomes in accordance with the present invention include a light sensitive lipid which has an absorbtivity of light at a predetermined wavelength and which forms a modified light sensitive lipid in response to sufficient light at the predetermined wavelength. The modified light sensitive lipid adjusts the lipid membrane of the light sensitive liposome from an encapsulating position to a releasing position.

The light sensitive lipid may be the sole lipid forming the lipid membrane of the inventive light sensitive liposomes, or may be one of a plurality of lipid compounds forming the lipid membrane. The other lipids may include the known, naturally occuring or synthetic lipids. In either instance, the light sensitive lipid is a structural component of the lipid membrane and contributes to the structural integrity of the lipid membrane. A preferred light sensitive liposome embodiment is wherein the light sensitive lipid constitutes at least about 50 wt. % of the lipid membrane, ad more preferably constitutes from about 75 wt. % to about 100 wt. %.

The polar head regions of suitable light sensitive lipids for the present invention may be any of the various known lipid polar heads. For example, among the many suitable moieties esterified to the phosphoric acid portion of phosphoglycerides, are those such as $-CH_2CH_2NH_2$, $-CH_2CH_2N^+(CH_3)_3$, $-CH_2CHNH_2COOH$, $-CH_2CHOHCH_2OH$,

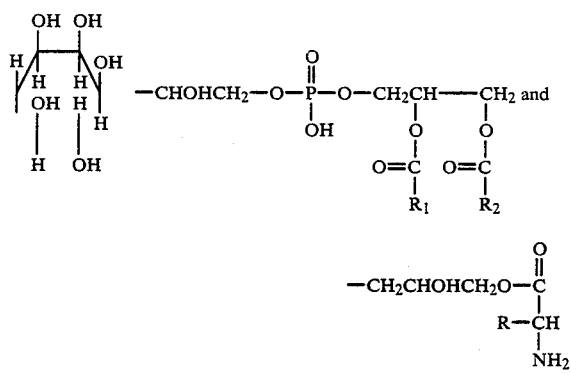

(Where R, $R_1$ and $R_2$ traditionally represent alkyl groups).

Suitable light sensitive lipids for the present invention include at least one retinoyl group located in the nonpolar tail region thereof. The light sensitive lipid may include two retinoyl groups in the nonpolar tail region, for reasons which will be further discussed hereinafter. Thus, for example, the light sensitive lipid may be a glycerol derivative having a retinoyl group at the 1 position carbon thereof and a retinoyl group at the 2 position carbon thereof. However, under certain uses the inventive light sensitive lipid can be a glycerol derivative having only one retinoyl group esterified at either the 1 position carbon, at the 2 position carbon, or mixtures thereof.

A representative light sensitive lipid having two retinoyl groups esterified at the 1 and 2 position carbons of a glycerol derivative is illustrated by FIG. 1, below, and a representative glycerol derivative having a single retinoyl group esterified at the 2 position carbon of a glycerol derivative is illustrated by FIG. 2, below.

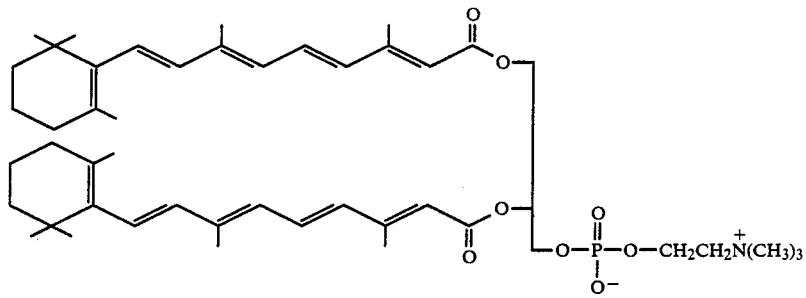

FIGURE 1

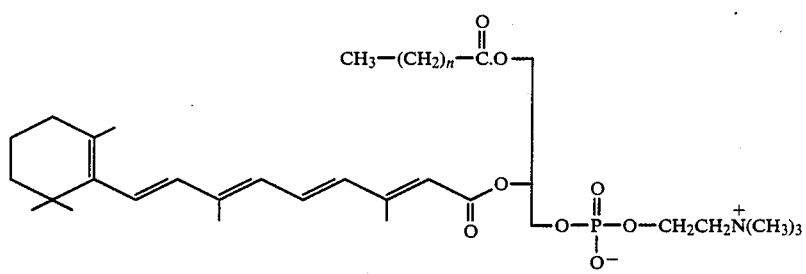

FIGURE 2

The FIG. 1 structure is di-retinoyl-sn-glycero-3-phosphocholine (sometimes hereinafter referred to as DRPC). Where n=14 the FIG. 2 structure is 1-palmitoyl, 2-retinoyl-sn-3-phosphocholine (which will sometimes hereinafter be referred to as PRPC). The fatty acid chain in the nonpolar tail region of the FIG. 2, illustrative structure, can vary. For example, n of the $-(CH_2)_n-$ FIG. 2 illustrative structure, can be various integers, most usually wherein n is from about 8 to about 18, or such a chain may include one or more double bonds, either conjugated or non-conjugated; and, as already discussed the moiety esterified to the phosphoric acid portion of the polar head regions can take a variety of forms.

Both the DRPC and the PRPC compounds are known, and can be prepared by conventional techniques. DRPC may be synthesized with the slight modification that benzene instead of dimethylsulfoxide is used to transfer the intermediate, retinoylimidazolide, to the reaction mixture. The PRPC and DRPC, when isolated, are preferably stored at $-20°$ C. in sealed ampules under argon in $CHCl_3$ that has been passed over neutral aluminum oxide.

It is preferred that preparation of the light sensitive lipid for use in forming the inventive light sensitive liposomes be prepared at least in part, more preferably in major part, from transretinoic acid. For example, in preparing a suitable light sensitive lipid for the present invention it is preferable that the retinoic acid used as the precursor for the at least one retinoyl group be at least standardized as to the relative quantities of trans and the various cis isomers, by means such as HPLC.

The FIGS. 1 and 2 structures, above may be formed as generally illustrated by the respective Reaction Schemes I and II, below.

REACTION SCHEME I
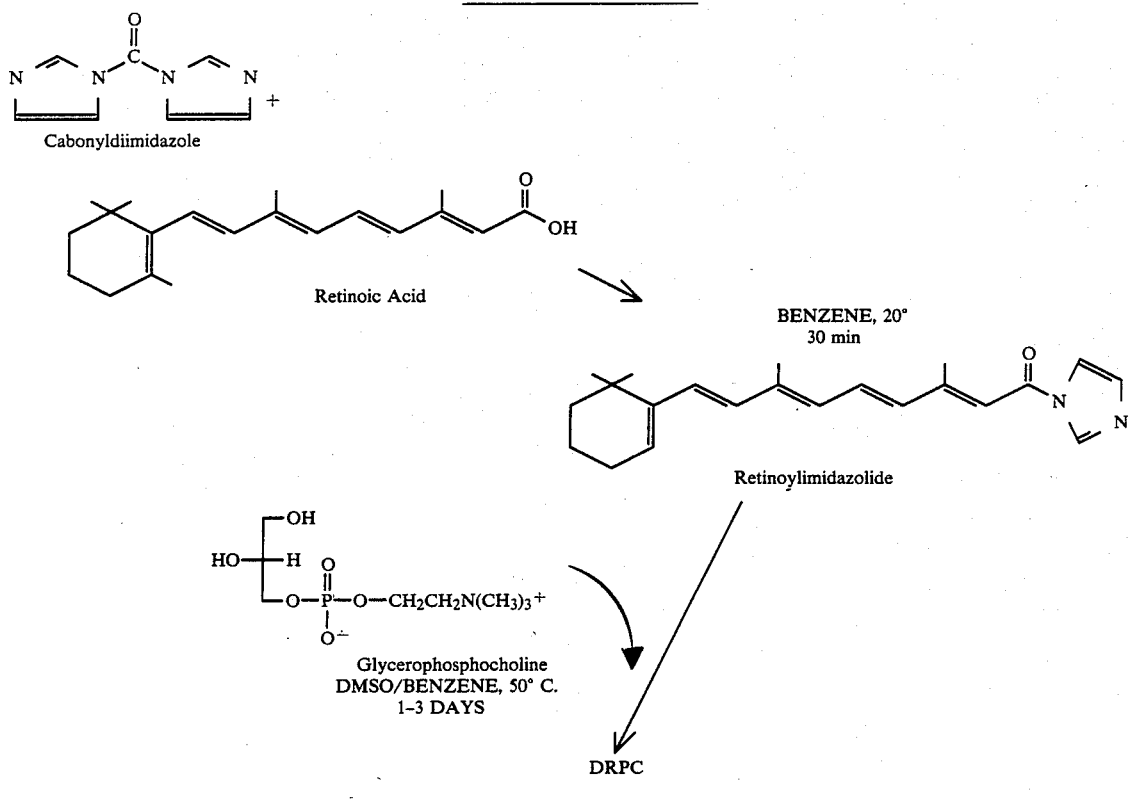
REACTION SCHEME II
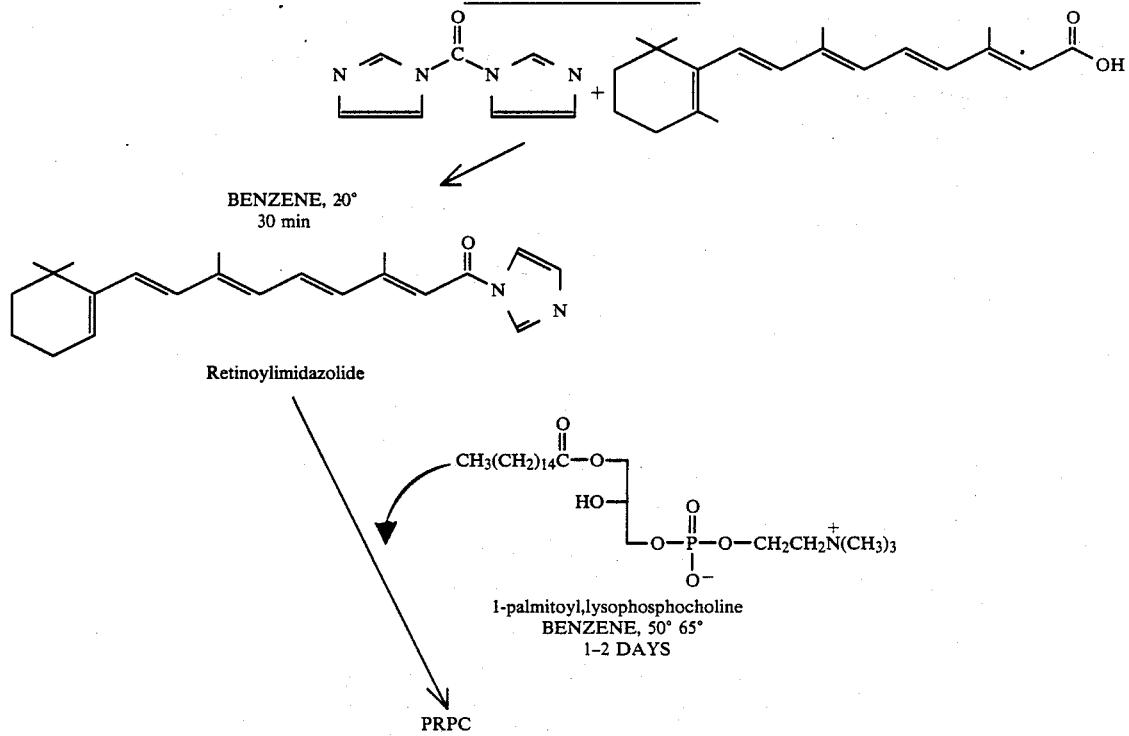
The relative sensitivity of the DRPC isolated from the Reaction Scheme I, above, to irradiation is substantially similar with respect to the retinoic acid starting material. There is little difference in the wavelength maximum (based upon UV absorption spectra) between DRPC and retionic acid, but both compounds are quite sensitive to irradiation. For example, after sixty seconds of irradiation, the percent decrease in the O.D. at 366 nm is 38.1% for DRPC and 27.4% for retionic acid. It is believed that the retinoyl group(s) of the light sensitive lipid, when irradiated with the appropriate wavelength of light, gives rise to a variety of geometric isomers, such as cis configurations of the retinoyl group(s).

In any event, in response to sufficient light at a predetermined wavelength the light sensitive lipid forms a modified light sensitive lipid and adjusts the lipid membrane of the inventive light sensitive liposomes from an encapsulating position for a fluid to a releasing position. In the releasing position, the previously encapsulated fluid may leak from the lipid membrane.

In the best mode contemplated for practice of the present invention, the lipid membrane of the inventive light sensitive liposome permits substantially all of the fluid to leak from the lipid membrane, or exchange with the outside—usually aqueous—environment, in response to sufficient irradiation at the predetermined wavelength. That is, sufficient irradiation permits the previously separated fluid to communicate with the medium outside the membrane. The predetermined wavelength is normally determined by the particular light sensitive lipid. With DRPC and PRPC the wavelength is preferably from about 300 nm to about 400 nm, more preferably is about 360 nm. The preferred sufficient irradiation is an irradiance of at least about 4, more preferably about 4.5 to about 5, mW/cm$^2$ for at least about 15 seconds.

For particular applications it may be desirable that the inventive light sensitive liposomes release less than their entire contents, or that they release all (or part) of their contents over periods of time greater than 60 seconds. Less than 100% release, or slower release, situations may be achieved in various ways, for example, may be achieved by decreasing the mole percent of the light sensitive lipid in the lipid membrane (e.g. by including one or more non-light sensitive lipids in forming the lipid membrane), by reducing the intensity of irradiation, or by decreasing the duration of irradiation.

EXPERIMENTAL

Example I

Seven light sensitive liposome compositions were prepared as described by (a) through (f) below. The fluid which was encapsulated for all seven compositions included carboxyfluorescein. The seven compositions were all stored at 6° C. until each monitoring experiment was performed.

Briefly, the monitoring method involved monitoring the increase in fluorescence as fluid leaks out of the vesicles. Because of self quenching, the fluorescence of a photosome suspension with 100 mM fluorescein encapsulated can be as low as 2% to 3% of the fluorescence when all the dye has leaked from the vesicles. For each experiment, a 3 ml aliquot of the diluted light sensitive liposomes was pipetted into a cuvette. The amount of leakage at varous times were estimated by Equation (1), where F(t) is the observed fluorescence at time t, F(t=$\phi$) is the background fluoresence at the beginning of the experiment and F(t=$\infty$) corresponds to the fluorescence obtained by adding to the fluorometer cell 0.1 ml of a 100% Triton-X solution which lysed the photosomes allowing all the carboxyfluorescein to leak out.

$$\% \text{ Leakage} = \frac{F(t) - F(t = 0)}{F(t = \infty) - F(t = 0)} \times 100 \quad \text{Eq. 1:}$$

For each experiment the fluorometer was set to read 100% with the F(t=$\infty$) value. Fluorescence was measured on a Perkin-Elmer MPF-2A Fluorescence Spectrophotometer equipped with a circulating water bath that controlled temperature.

(a) Light sensitive liposomes, with DRPC as the lipid membrane, were formed by the "mechanical dispersal" method. A quantity of DRPC was dried in a 100 ml round bottom flask, and then dispersed in 100 mM carboxyfluorescein at 38° C. by gentle shaking. The dispersion was allowed to equilibrate to room temperature, and the light sensitive liposomes formed therefrom were applied to a column of suitable gel filtration medium, to separate the unencapsulated carboxyfluorescein from the light sensitive liposome vesicles. The light sensitive liposomes were collected from the column in a 50 ml volumetric flask, and brought to volume with phosphate buffered saline composed of 11.08 mM NaH$_2$PO$_4$, 23.43 mM Na$_2$HPO$_4$ and 77.0 mM NaCl.

(b) Light sensitive liposomes, with DRPC as the lipid membrane, were formed by the "mixed phase, or ethanol injection", method. A quantity of DRPC was dissolved in a small volume of ethanol which was then injected directly into a rapidly stirring aqueous solution of 100 mM carboxyfluorescein. The light sensitive liposomes formed therefrom were separated from unencapsulated carboxyfluorescein by gel filtration.

(c) Light sensitive liposomes, with PRPC as the lipid membrane, were formed by the mechanical dispersal method, separated and stored as described in (a), above.

(d) Light sensitive liposomes, with PRPC as the lipid membrane, were formed by the mixed phase method as described in (b), above, and then separated and stored as described in (a), above.

(e) Light sensitive liposomes, with the lipid membrane being formed of 90 wt. % PRPC and 10 wt. % Vitamin E, were formed by the mechanical dispersal method, and separated as described in (a), above.

(f) Light sensitive liposomes, with the lipid membrane being formed of 90 wt. % PRPC and 10 wt. % Vitamin E, were formed by the mixed phase method as described in (b), above, then separated as in (a), above.

The seven light sensitive liposome preparations (a)-(f) were irradiated with a constant output of about 5 mW/cm$^2$ at room temperature. The irradiation was of light with a wavelength maximum of 360 nm. The data of Table I, below, represents the % leakage of carboxyfluorescein from the respective liposome preparations as a function of seconds of irradiation.

TABLE I

| Light Sensitive Liposome Preparation | Seconds of Irradiation | % leakage |
| --- | --- | --- |
| (a) | 5 | 0 |
|  | 10 | 10 |
|  | 15 | 40 |
|  | 20 | 85 |
|  | 30 | 100 |
| (b) | 15 | 0 |
|  | 25 | 15 |
|  | 35 | 45 |
|  | 45 | 90 |
|  | 50 | 95 |
|  | 60 | 100 |
| (c) | 30 | 0 |
|  | 60 | 30 |
|  | 90 | 85 |

TABLE I-continued

| Light Sensitive Liposome Preparation | Seconds of Irradiation | % leakage |
| --- | --- | --- |
|  | 120 | 90 |
| (d) | 30 | 0 |
|  | 60 | 25 |
|  | 90 | 85 |
|  | 120 | 85 |
| (e) | 90 | 3 |
|  | 180 | 5 |
|  | 250 | 20 |
|  | 350 | 75 |
|  | 450 | 85 |
| (f) | Substantially as for (e) | |

As the data of Table I, above, illustrates, light sensitive liposomes formed with two retinoyl groups per light sensitive lipid (e.g. the DRPC liposomes of (a) and (b), above) provided with 100% release of the encapsulated contents in about 30–60 seconds, whereas light sensitive liposomes formed with one retinoyl group per light sensitive lipid (e.g. the PRPC liposomes of (c) and (d), above) provided about 85% release of the encapsulated contents in about 120 seconds. The light sensitive liposomes formed as in (e) and (f), above, required about 450 seconds for about 85% release. This is believed due at least partly to the fact that the Vitamin E content reduced the concentration of retinoyl groups available.

Example II

The inventive light sensitive liposomes are particularly useful for selectively adding a fluid to a cell by contacting the inventive light sensitive liposomes with one or more cells and irradiating thhe light sensitive liposome and cell or cells to release the encapsulated fluid. This is illustrated as follows.

The light sensitive liposome composition was prepared from a mixture of DRPC, LRPC (lysoretinoyl-sn-3-glycerophosphocholine), tocopherol and BHT, wherein the four components were in a ratio of 1:1:1:0.15. The starting components were formed into light sensitive liposomes by ethanol injection in an isotonic buffer including 6-mercaptopurine riboside (6-MPR). The light sensitive liposomes so prepared were separated from unencapsulated 6-MPR by chromatography. Another batch of light sensitive liposomes, but without 6-MPR in the encapsulated fluid, was prepared as control light sensitive liposomes.

Preparations of S49 cells in the log growth phase were divided into 6 cell samples. The first cell sample was a control cell sample. The second cell sample was admixed with the control light sensitive liposomes. The third cell sample was admixed with 240 μm 6-MPR. The fourth cell sample was admixed with the light sensitive liposomes having 6-MPR encapsulated therein. The fifth cell sample was admixed with 240 μm 6-MPR and control light sensitive liposomes. An aliquot was then taken from each of the five cell samples and irradiated for 5 minutes (360 nm, 5 mW/cm$^2$). The non-irradiated and the irradiated portions of the five cell samples were then separately incubated at 37° C. in a standard growth medium for 2 hours. The cells were isolated, washed, and resuspended in a drug free media for 48 hours, and then examined for growth rate. The normal growth rate of S49 cells is at about an 18 hour doubling time, which is known to be described two-fold (ED50) by 240 μm 6-MPR. The results are illustrated by Table II, below.

TABLE II

| Cell Samples | Generation time (hours) |
| --- | --- |
| first, not irradiated | 18 ± 2.7 |
| first, irradiated | 21 ± 3.15 |
| second, not irradiated | 23 ± 3.45 |
| second, irradiated | 30 ± 4.5 |
|  | ED50 (μm) |
| third, not irradiated | 240 |
| third, irradiated | 220 |
| fourth, not irradiated | >1000 |
| fourth, irradiated | 0.8 |
| fifth, not irradiated | 190 |
| fifth, irradiated | 175 |

As may be seen from Table II, above, the control light sensitive liposomes were mildly toxic to the cells, and irradiation increased the toxicity. The data from the fourth cell sample illustrated that encapsulation of 6-MPR in the light sensitive liposomes significantly protected the cells from 6-MPR cytotoxicity in the dark, and that upon release of the encapsulated contents following irradiation the effectiveness of the drug was increased 275-fold over unencapsulated 6-MPR.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A light sensitive liposome comprising:
a lipid membrane, said lipid membrane encapsulating a fluid, said lipid membrane including a light sensitive lipid in an amount from about 50 wt.% to about 100 wt.% of the lipid membrane and having a polar head region and a nonpolar tail region, said light sensitive lipid including one retinoyl group or two retinoyl groups covalently bonded in the nonpolar tail region of said light sensitive lipid, said light sensitive lipid having an absorptive of light at a predetermined wavelength between about 300 nm to about 400 nm, said light sensitive lipid providing release of said fluid from said lipid membrane in response to an effective amount of irradiation at said predetermined wavelength.

2. The light sensitive liposome as in claim 1 wherein:
said light sensitive lipid is a glycerol derivative defining a 1 position carbon and a 2 position carbon, said one retinoyl group esterified at said 1 position carbon or at said 2 position carbon and said two retinoyl groups esterified at both of said 1 and 2 position carbons.

3. The light sensitive liposome as in claim 1 wherein:
said retinoyl groups are derived in major part from transretinoic acid.

4. The light sensitive liposome as in claim 1 wherein:
said light sensitive lipid includes di-retinoyl-sn-glycero-3-phosphocholine, 1-palmitoyl, 2-retinoyl-sn-3-phosphocholine and mixtures thereof.

5. The light sensitive liposome as in claim 1 wherein said light sensitive lipid with one retinoyl group has the structure

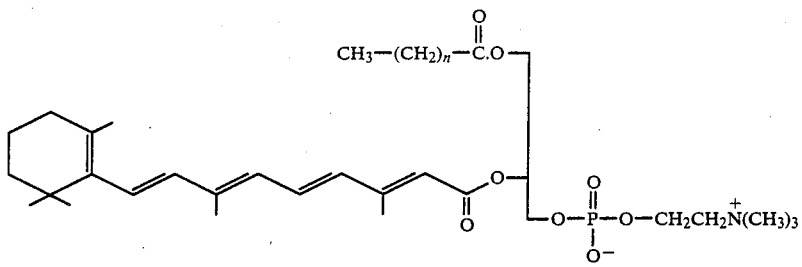

wherein n is from about 8 to about 18, and said light sensitive lipid with two retinoyl groups has the structure

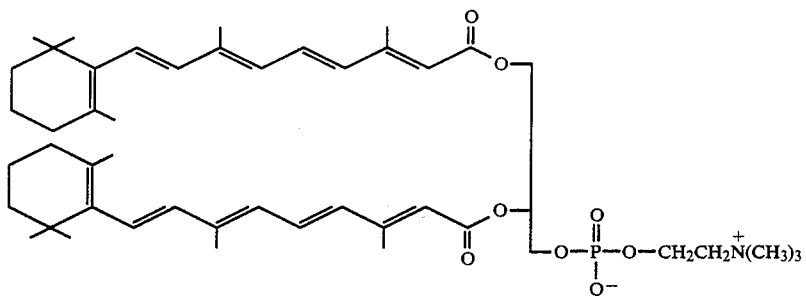

6. The light sensitive liposome as in claim 1 wherein said fluid includes a polar liquid phase.

7. The light sensitive liposome as in claim 6 wherein said polar liquid phase is aqueous.

8. The light sensitive liposome as in claim 6 wherein said fluid includes a biologically active component.

9. The light sensitive liposome as in claim 6 wherein said fluid includes a pharmaceutical.

10. The light sensitive liposome as in claim 1 wherein: said membrane in the releasing position permits substantially all of said fluid to leak therefrom.

11. The light sensitive liposome as in claim 1 wherein said light sensitive lipid is a structural component of said lipid membrane.

12. The light sensitive liposome as in claim 4 wherein said predetermined wavelength is about 360 nm.

13. The light sensitive liposome as in claim 12 wherein the effective amount of said irradiation permits substantially all of said fluid to leak from said membrane within about 60 seconds.

14. The light sensitive liposome as in claim 13 wherein said effective amount of irradiation is an irradiance of at least about 4 mW/cm$^2$ for at least about 15 seconds.

15. The light sensitive liposome as in claim 1 wherein said light sensitive lipid with one retinoyl group has the structure

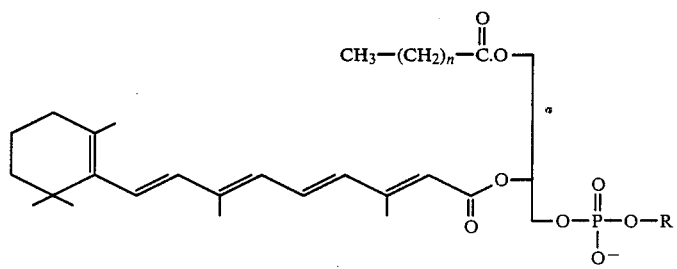

and said light sensitive lipid with two retinoyl groups has the structure

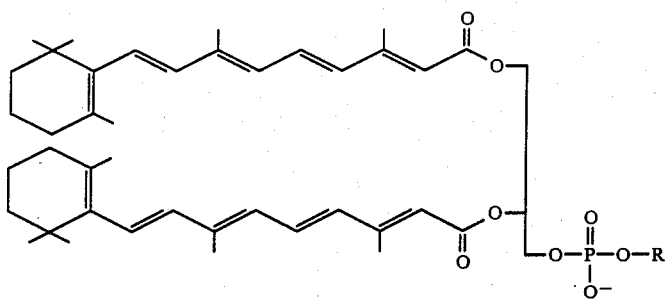
wherein n is about 8 to about 18, and R is selected from the group consisting of —H, —CH$_2$CH$_2$NH$_2$, —CH$_2$CH$_2$N$^+$(CH$_3$)$_3$, —CH$_2$CHNH$_2$COOH, —CH$_2$CHOHCH$_2$OH, and
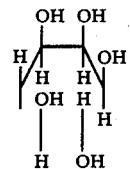
* * * * *

UNITED STATES PATENT AND TRADEMARK OFFICE
CERTIFICATE OF CORRECTION

PATENT NO. : 4,882,165

DATED : NOVEMBER 21, 1989

INVENTOR(S) : HUNT et al

It is certified that error appears in the above-identified patent and that said Letters Patent is hereby corrected as shown below:

Column 14, in Claim 15: replace " 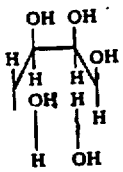 " with — 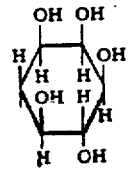 —

Signed and Sealed this

Eighteenth Day of September, 1990

Attest:

HARRY F. MANBECK, JR.

*Attesting Officer*          *Commissioner of Patents and Trademarks*